(12) United States Patent
Miles et al.

(10) Patent No.: US 6,858,748 B1
(45) Date of Patent: Feb. 22, 2005

(54) TREATMENT OF COLON CANCER

(75) Inventors: D. Howard Miles, Winter Springs, FL (US); Solodnikov Sergey Yurjevich, Perm (RU); Krasnykh Olga Petrovna, Perm (RU); Lisovskaja Natalja Anatoljevna, Perm (RU); Elena A. Goun, Stanford, CA (US)

(73) Assignee: Research Foundation of the University of Central Florida, Orlando, FL (US)

( * ) Notice: Subject to any disclaimer, the term of this patent is extended or adjusted under 35 U.S.C. 154(b) by 0 days.

(21) Appl. No.: 10/756,731

(22) Filed: Jan. 13, 2004

Related U.S. Application Data

(62) Division of application No. 10/164,879, filed on Jun. 7, 2002.
(60) Provisional application No. 60/296,823, filed on Jun. 8, 2001.

(51) Int. Cl.[7] ............................................. C07C 229/00
(52) U.S. Cl. ...................... 560/169; 560/156; 560/174; 560/205; 560/219; 560/226
(58) Field of Search ................................. 560/156, 174, 560/205, 219, 226, 169; 423/407; 149/36; 564/310

(56) References Cited

U.S. PATENT DOCUMENTS

| | | | |
|---|---|---|---|
| 3,862,954 A | 1/1975 | Omodei-Sale | 260/296 |
| 5,274,002 A | 12/1993 | Hawkins | 514/530 |
| 5,308,852 A | 5/1994 | Girard | 514/336 |
| 5,334,612 A | 8/1994 | Kalden | 514/440 |
| 6,048,896 A | 4/2000 | Giordani | 514/545 |
| 6,066,670 A | 5/2000 | Brown | 514/557 |
| 6,080,790 A | 6/2000 | Boyd et al. | 514/650 |
| 6,121,450 A | 9/2000 | Jones | 546/81 |
| 6,180,651 B1 | 1/2001 | Nicolai | 514/336 |
| 6,232,312 B1 | 5/2001 | Pamukcu | 514/237.5 |

*Primary Examiner*—Johann R. Richter
*Assistant Examiner*—Karl Puttlitz
(74) *Attorney, Agent, or Firm*—Brian S. Steinberger; Law Offices of Brian S. Steinberger, P.A.

(57) ABSTRACT

The novel compound of the disclosure is 4-chloro-4-(4-ethoxy-phenyl)-2-(fluoren-9-ylidene-hydrazono)-but-3-enoic acid methyl ester (3F-19), and it alone or in combination with 4-(4-Ethoxy-phenyl)-2-(N'-fluoren-9-ylidene-hydrazino)-2-hydroxy-4-oxo-butyric acid methyl ester (OF-13), appears useful in humans as therapeutic means for the eradication of tumors from the human's colon.

4 Claims, 1 Drawing Sheet

3F-19

TREATMENT OF COLON CANCER

FIELD OF THE INVENTION

This is a Divisional of application Ser. No. 10/164,879 filed Jun. 7, 2002, and this invention relates to the use of novel compounds alone or in combination or treatment of human colon cancer and claims the benefit of priority of U.S. Provisional Application Ser. No. 60/296,823 filed Jun. 8, 2001.

BACKGROUND OF THE INVENTION

Cancer is a global killer of humans with breast cancer and colon cancer among the leaders with many other types killing modest amounts of humans yearly. Breast cancer is the primary killer of women. Colon cancer is the third greatest killer of people in the United States.

Colon cancer although having an excellent cure rate is a very common cancer second only to lung cancer in the United States. 129,400 new cases of colorectal cancer were estimated for 1999 with 56,600 deaths therefrom. The strongest risk factor for colon cancer is age. The incidence rates rise from 10 per 100,000 at age 40-45 to 300 per 100,000 at age 75-80. The cumulative life time risk for the disease is 1 in 20. Men are more likely to develop colon cancer than women. Black Americans are more likely than white Americans to be diagnosed with colorectal cancer. Smokers, drinkers, sedentary, and obese persons are more likely to develop colon cancer.

The U.S. patent literature has many disclosures of oxo-butenoic (crotonic) compounds:

Pamukci (U.S. Pat. No. 6,232,312) describes crotonic acid derivatives (column 22, lines 43–58) for the treatment of colonic polyps;

Jones et al (U.S. Pat. No. 6,121,450) discloses crotonic acid derivatives (column 8, line 34; column 78, line 24 and at example 34 as steroid modifiers in treating breast cancer (column 1, lines 55–58);

Kalden, et al (U.S. Pat. No. 5,334,612) discloses compounds said to be useful for treating AIDS including derivatives of carboxylic acid (column 9, line 31) and pyrrolidine (column 7, line 24);

Brown (U.S. Pat. No. 6,066,670) describes an anti-viral admixture containing crotonic acid for treating tumors (see Abstract);

Horwell, et al (U.S. Pat. No. 5,580,896) discloses many 4-oxo-2-butenoic acid derivatives (column 13, lines 21–59; also in columns 15+, examples 25, 26, 32, 34, 40, 43–46, 77–79, 97, 99, 103, 106,), which are useful for inhibiting colorectal cancer, i.e., colon cancer (Abstract);

Giordani, et al (U.S. Pat. No. 5,580,890) discloses 4-oxo-2-butenoic acid derivatives said to be useful for treatment of AIDS (column 1, line 8 and column 2, line 61; and, Yonemeto, et al (U.S. Pat. No. 6,083,985) recites a number of anti-tumor or anti-AIDS agents that include butenoic acid derivatives.

The U.S. patent literature has many disclosures of butanoic acid derivatives including:

Nicolai, et al (U.S. Pat. No. 6,180,651) discloses many anti-inflammatory and analgesic compounds, including adenocarcinoma (column 1, line 55), which includes heterocyclic alcohol-esters (column 11, lines 1–16) and butanoic acid derivatives (many Examples including 47 through 162);

Girard, et al (U.S. Pat. No. 5,308,852) discloses many compounds including butanoic acid derivatives (see Methods B and C of schemes II and III) which compounds which are said to inhibit tumor metastasis (column 7, line 56 and column 8, line 4);

Frechette (U.S. Pat. No. 5,696,117), Frechette (U.S. Pat. No. 5,854,242) and Frechette (U.S. Pat. No. 5,707,990) describe 148 benzoxazine and pyrido-oxazine heterocyclic as anti-bacterial compounds;

Omedi-Sale (U.S. Pat. No. 3,862,954) shows tri-azole compounds for CNS use;

Hawkins (U.S. Pat. No. 5,274,002) describes many analogs of phenyl ethers of a substituted phenyl of the formula structure at column 1, lines 49–60 with 37 examples of specific compounds which compounds may be useful for tumor inhibition (column 22, line 64); and, Boyd, et al (U.S. Pat. No. 6,080,790) also describes many tri-substituted phenyl derivatives according to the formula of the Abstract with 15 examples of specific compounds which may be useful for malignant skin diseases (column 5, line 46).

It appears from a review of the foregoing patents that neither the 2-hydrazino-3-oxo-butenoic acid nor the 2-hydroxy-4-oxobutyric acid derivatives of interest are disclosed and thus there is no report of their activity against human colon cancer.

Consequently, there is a need for an anti-cancer drug for humans that mitigate the above mentioned disadvantages of current drug therapy and effectiveness against the identified human colon cancer.

SUMMARY OF THE INVENTION

The first objective of the present invention is to provide a novel drug effective for treatment of human colon cancer.

Another object of this invention is to provide a novel 2-hydrazino-3-oxo-butenoic acid derivative.

A preferred embodiment of the invention encompasses the specific compounds: 4-Chloro-4-(4-ethoxy-phenyl)-2-(fluoren-9-ylidene-hydrazono)-but-3-enoic acid methyl ester (3F-19), and the use of it and/or 4-(4-Ethoxy-phenyl)-2-(N'-fluoren-9-ylidene-hydrazino)-2-hydroxy-4-oxo-butyric acid methyl ester (OF-13) in humans as therapeutic means for the eradication of tumors from the human's colon.

Further objects and advantages of this invention will be apparent from the following detailed description of presently preferred embodiments, which are illustrated structurally in the accompanying drawings.

DESCRIPTION OF THE PREFERRED EMBODIMENTS

Before explaining the disclosed embodiments of the present invention in detail, it is to be understood that the invention is not limited in its application to the details of the particular arrangement shown since the invention is capable of other embodiments. Also, the terminology used herein is for the purpose of description and not of limitation.

Figure 1:
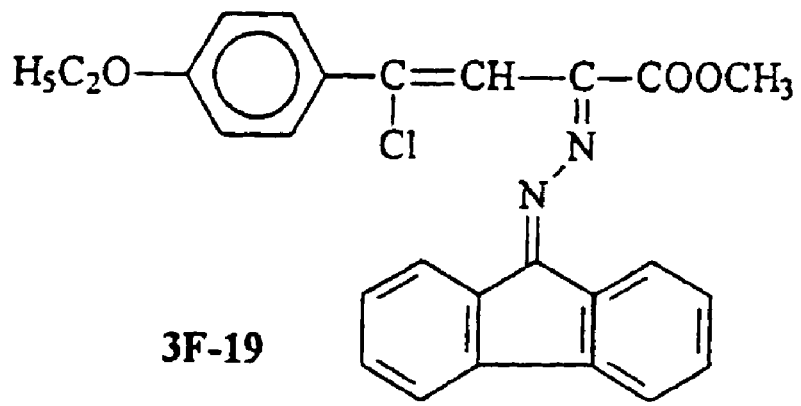
FIG. 1 illustrates structurally a chemical compound designated as 3F-19.
Figure 2:
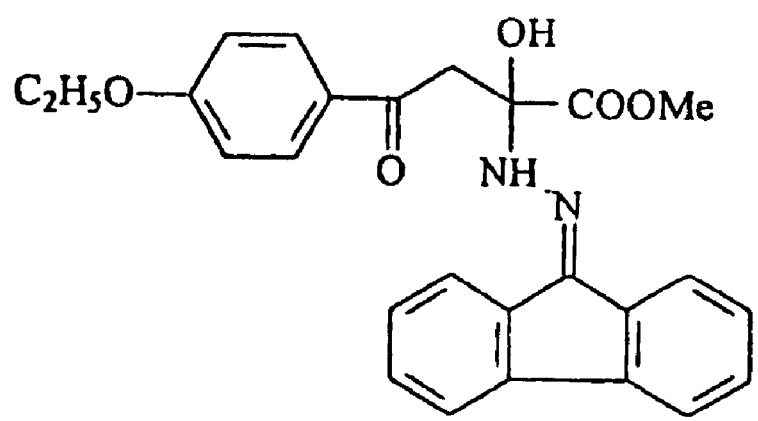
FIG. 2 illustrates structurally a chemical compound designated as OF-13.

As earlier recited this application has been filed in order to both disclose the novel 2-hydrazino-3-oxo-butenoic acid derivative structurally shown in FIG. 1 as well as the use of the structure in FIGS. 1 and/or 2 for biological activity useful for the treatment of human colon cancer. More specifically this application discloses the anti-tumor compounds: 4-Chloro-4-(4-ethoxy-phenyl)-2-(fluoren-9-ylidene-hydrazono)-but-3-enoic acid methyl ester (3F-19); and, 4-(4-Ethoxy-phenyl)$_2$—(N'-fluoren-9-ylidene-hydrazino)-2-hydroxy-4-oxo-butyric acid methyl ester (OF-13).

To facilitate a fill understanding of the invention:
the compound designated as 3F-19 is 4-Chloro-4-(4-ethoxy-phenyl)-2-fluoren-9-ylidene-hydrazono)but-3-enoic acid methyl ester; and the compound designated as OF-13 is 4-(4-Ethoxy-phenyl)-2-N'-fluoren-9-ylidene-hydrazino)-2-hydroxy-4-oxo-butyric acid methyl ester.

These compounds have very high activity against colon cancer and a very low toxicity as a ($LD_{50}$) in animals. The percent activity and animal toxicity for each compound is as follows:

3F-19 (100% against human colon cancer and $LD_{50}$>200 mg/kg); and,

OF-13 (100% against human colon cancer and $LD_{50}$>1500 mg/kg).

Preparation of (3F-19)

EXAMPLE 1

The preparation of 4-Chloro-4(4-ethoxy-phenyl)-2-(fluoren-9-ylidene-hydrazono)-but-3-enoic acid methyl ester (3F-19) To the solution of 10 g (0.0026 moles) of 4-(4-Ethoxy-phenyl)-2-(N'-fluoren-9-lidene-hydrazino)-4-oxo-but-2-enoic acid methyl ester (1) (synthesis was previously published by Konyukhova, N. A. Krasnykh, O. P.; Aliev, Z. G.; Maslivets, A. N. *Chemistry of Heterocyclic Compounds* (New York, N.Y., United States)(Translation of *Khimiya Geterotsiklicheskikh Soedinenii*) (2001), 37(6), 779–780) in 5 mL of anhydrous benzene 0.3935 g (0.0031 moles) oxalyl chloride was added. The reaction mixture was refluxed for 1 hour 40 min, cooled, the precipitate was filtered and recrystallized from absolute benzene to give 0.62 g (54%) of yellow crystals, m.p. 163—163 (decomp).

Preparation of OF-13

EXAMPLE 2

The preparation of 4(4-Ethoxyphenyl)-2-(N'-fluoren-9-ylidene-hydrazino)-2-hydroxy-4-oxobutyric acid methyl ester (OF-13). A solution of 5.0 g (0.02 moles) of methyl 4-p-ethoxyphenyl-2-hydroxy-4-oxo-2-butenoate (1) and 3.88 g (0.02 moles) of fluorene-9-ylidene-hydrazine (2) in 80 mL of absolute benzene and absolute toluene (1:1) was refluxed for 1 hr 30 min with a Dean-Stark trap (the end of the reaction was determined by TLC), cooled and the precipitate was filtered and recrystallized from benzene-diethyl ether-hexane mixture (1:3:2) to give 2.65 g (53% yield) of colorless crystals with mp 114–116° C.

Solubility: highly soluble in DMSO, DMFA, dichloroethane, acetonitrile, insoluble in hexane. The compound is not stable in solutions and decomposes quickly when the solution is heated or stored for a long time with the formation of OF-12.

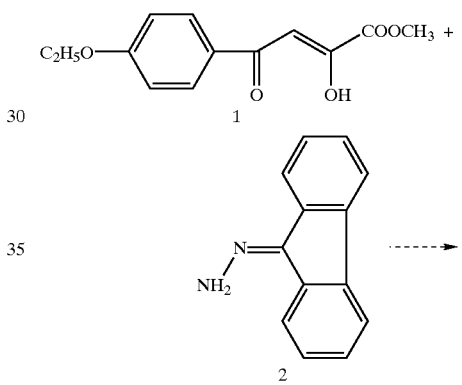

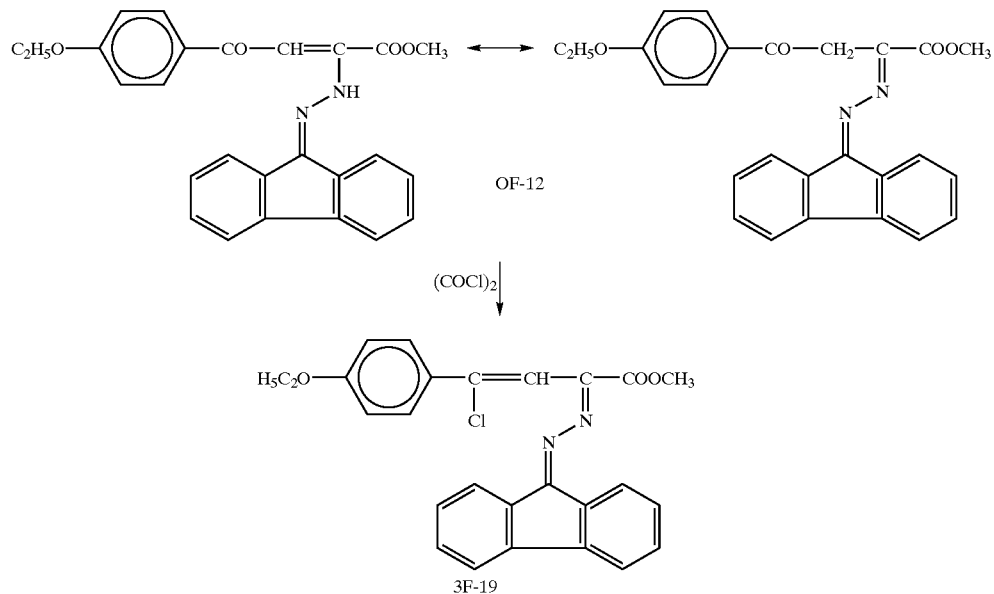

-continued

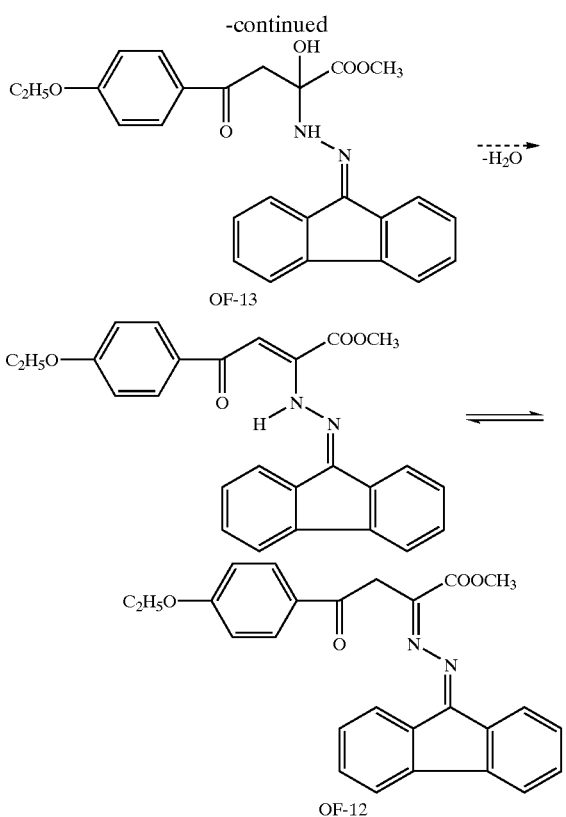

It is seen from the above that (OF-13) is an intermediate product during the synthesis of (OF-12).

Cytotoxicity Assay.

The antitumor activity against human colon cancer cells of the novel compounds (as earlier reported) was realized by the following procedure which determines the inhibitory effect of test samples on the growth of human colon cancer cells (ATCC CCL220). The CCL220 cells are grown in RPMI 1640 media+10% Fetal bovine serum+1% Antibiotic/Antimycotic for approximately 48 hours at 37° C./5% $CO_2$ in the presence of the test compound.

Growth/Non-Growth of the cells (e.g., cell density) is determined using Promega's MTS/PMS assay system. MTS (3-(4,5-dimethylthiazol-2-yl)-5-(3-carboxymethoxyphenyl)-2-(4-sulfophenyl)-2H-tetrazolium, inner salt) is an aqueous compound that is reduced to soluble formazan by the presence of NADH formed by dehydrogenases present within the CCL220 cells. The absorbance of the formazan can be measured at 490 nm and is directly proportional to the number of living cells present in the culture. PMS (Phenazine Methosulfate) is added an electron coupling reagent and greatly increases the rate of reduction.

To facilitate a full understanding of the procedure the following definitions are offered:

Test wells—wells containing test sample and Diluted CCL220 cells
Test values—absorbance of test wells
Blank wells—wells containing test sample and CCL220 media (C220-01S); used to obtain background absorbance due to test sample
Blank values—absorbance of blank wells
Negative Control—maximal cell growth; results of test samples will be expressed as a percent of the Negative Control
Positive Control—known inhibitor of CCL220 cells; used to validate assay system
Matrix—solvent that the samples are prepared/diluted in
Assay samples of similar origin and matrix (e.g., methanol extraction, methylene chloride extraction, water soluble samples, etc.) together on the same plate in order to reduce the number of steps performed per plate.
Blank values will be determined for each sample to account for any color contribution due to the sample itself. These blank wells must contain the same amount of sample plus CCL220 media (no cells). After completion of MTS/PMS reaction blank values will be subtracted from the test value to obtain a net absorbance that will be used to calculate cell density.

All results are based upon a comparison to the Negative Control value of the plate. The Negative Control must contain the same amount of matrix (e.g., solvent) to offset any destructive effect the matrix may have on the growth of the CCL220 cells (allows for baseline values to be set).

For most samples, a CCL220 cell growth (initial density of 120,000 to 160,000 cells/ml) of approximately 48 hours followed by and incubation of 2 hours with the MTS/PMS Reagent is optimal.

In order to establish the accuracy of this assay a Positive Control consisting of 50 $\mu$M Methotrexate should not decrease the net absorbance to less than 90% of the Negative Control (CCL220 cells are somewhat resistant to methotrexate) is utilized.

Animal Toxicity Bioassay

Acute toxicity was studied on white mice of both sexes with weight ranging between 18–26 grams under intraperitoneal injection of 2% solution of tested compound in starch (the compound was dissolved in starch slime and injected) on the basis of 0.1 ml of solution per 10 g of the animal weight Each dose was tested on the group of 6 animals that were observed during 14 days period. (This method was approved by the Pharmacology committee of Russian Ministry of Health and has been widely used since 1968.) Averaged lethal dose ($LD_{50}$) of the compound was computed using results of experiments on 5–7 groups of animals using method of Litchfield and Wilkinson. (Belenkii M. L. "Elements of quantative determination of the pharmacological effect," Leningrad, 1963, 71 pages).

Use of the Invention for Treatment of Human Colon Cancer

Due to their low toxicity data, the compounds described as useful in this invention can be used effectively in a pharmaceutical composition comprising a non-toxic effective amount of the referenced compound or mixture thereof and/or in a tautomeric form thereof or a pharmaceutically acceptable salt thereof or pharmaceutically acceptable solvate thereof, and a pharmaceutically acceptable carrier thereof.

For administration to man in the curative or prophylactic treatment of human colon cancer in vitro dosages of compound(s) and admixtures thereof the invention will generally be in the range of from 5 to 500 mg daily for an average adult patient (70 kg). Thus for a typical adult patient, individual tablets or capsules contain from 2–500 mg of active compound, in a suitable pharmaceutically acceptable vehicle or carrier, for administration in single or multiple doses, once or several times per day. Dosages for intraveneous, buccal or sublingual administration will typically be within the range of from 5–1000 mg per single dose as required. The physician will determine the actual dosing regimen which will be most suitable for an individual patient by periodic colonoscope and/or anal blood examination to evaluate the tumor inhibitory effect of the compound(s) administered and it will vary with the age, weight and response of the particular patient.

The maximum human non-toxic one time administration dose for the compound(s) of the invention appears to 100–750 mg.

For human use, the compounds of the invention can be administered alone or jointly, but will generally be administered in admixture with a pharmaceutical carrier selected with regard to the intended route of administration and standard pharmaceutical practice. For example, they may be administered orally, buccally or sublingually, in the form of tablets containing excipients such as starch or lactose, or in capasules or ovules either alone or in admixture with excipients, or in the form of elixirs or suspensions containing flavouring or colouring agents. The compounds may also be injected parenterally, for example intraveneously, intramuscularly, subcutaneously or intracoronarily. For parenteral administration, they are best used in the form of a sterile aqueous solution which may contain other substances, for example enough salts or glucose to make the solution isotonic with blood.

The invention thus provides a method for the treatment of colon cancer in a human mammal which comprises administering an effective, non-toxic, amount of a compound according to the invention or a tautomeric form thereof and/or a pharmaceutically acceptable salt thereof and/or a pharmaceutically acceptable solvate thereof, to a: colon cancer invaded human mammal in need thereof.

ADVANTAGES OF THE INVENTION

Surgery is the primary treatment for colon cancer and the only treatment that can cure the patient. Adjuvant Chemotherapy means that you treat with chemotherapy after the operation that has removed all visible tumor tissue to kill single cancer cells or micro metastatic tumor deposits that may have spread from the primary tumor before or at the time of surgery through blood or lymph vessels to diminish the risk of clinically evident distant metastases. The effect of adjuvant chemotherapy after colon cancer has been debated for many years and many studies have been made, some not showing any benefit, but some showing a benefit. There is an increasing number of recent studies and meta analyses showing a positive effect on Stage III (node positive) colon cancer and also but not as well documented Stage III Rectal Cancer. The benefit for Stage II is still unclear. The increase in 5-year survival is in the range from 50% up to 65% for Stage III Colon Cancer. The drugs being used are 5-FU (fluorouracil)+Leucovorin or 5-FU+Levamisol. It should be mentioned that 5-FU drug has been already used for more than 30 years.

Toxicity of 5-FU drug in mice is IPN-Mice LD50 230 mg $kg^{-1}$. It should be compared with IPN-Mice 1500 mg $kg^{-1}$ toxicity of the claimed drug. Consequently the claimed drugs provide basis for the development of new drugs with less side effects and lower toxicity.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

We claim:

1. A mixture suitable for administration to a human being comprising 4-Chloro-4-(4-ethoxy-phenyl)-2-(fluoren-9-ylidene-hydrazono)-but-3-enoic acid methyl ester and 4-(4-Ethoxy-phenyl)-2-(N'-fluoren-9-ylidene-hydrazino)-2-hydroxy-4-oxo-butyric acid methyl ester having the property of anti-tumor activity against colorectal cancer.

2. A method of treating a human having colon cancer comprising the step of: administering an effective amount of 4-Chloro-4-(4-ethoxy-phenyl)-2-(fluoren-9-ylidene-hydrazono)-but-3-enoic acid methyl ester to said human.

3. A method of treating a human having colon cancer comprising the step of: administering an effective amount of 4-(4-Ethoxy-phenyl)-2-(N'-fluoren-9-ylidene-hydrazino)-2-hydroxy-4-oxo-butyric acid methyl ester to said human.

4. The method according to claim 3 further comprising administering an effective amount of 4-(4-ethoxy-phenyl)-2-(fluoren-9-ylidene-hydrazono)-but-3-enoic acid methyl ester.

* * * * *